United States Patent [19]

Powell et al.

[11] Patent Number: 5,447,525
[45] Date of Patent: Sep. 5, 1995

[54] PACEMAKER WHICH ADAPTS TO MINIMIZE CURRENT DRAIN AND PROVIDE DESIRED CAPTURE SAFETY MARGIN

[75] Inventors: Richard M. Powell, Bloomington; Steven L. Jensen, Andover, both of Minn.

[73] Assignee: Medtronic, Inc., Minneapolis, Minn.

[21] Appl. No.: 122,258

[22] Filed: Sep. 15, 1993

[51] Int. Cl.⁶ .................................... A61N 1/365
[52] U.S. Cl. .............................. 607/28; 607/27
[58] Field of Search .......................... 607/28, 27

[56] References Cited

U.S. PATENT DOCUMENTS

| | | | |
|---|---|---|---|
| 4,428,378 | 1/1984 | Anderson et al. | 128/419 |
| 4,485,813 | 12/1984 | Anderson et al. | 128/675 |
| 4,556,063 | 12/1985 | Thompson et al. | 128/419 |
| 4,729,376 | 3/1988 | DeCote, Jr. | 607/28 |
| 4,817,605 | 4/1989 | Sholder | 607/28 |
| 4,979,507 | 12/1990 | Heinz et al. | 607/28 |
| 5,127,402 | 7/1992 | Mann et al. | 607/28 |
| 5,127,404 | 7/1992 | Wyborny et al. | 128/419 |
| 5,154,170 | 10/1992 | Bennett et al. | 128/419 |
| 5,158,078 | 10/1992 | Bennett et al. | 607/27 |
| 5,226,413 | 7/1993 | Bennett et al. | 607/30 |
| 5,320,643 | 6/1994 | Roline et al. | 607/28 |

*Primary Examiner*—William E. Kamm
*Assistant Examiner*—Kennedy J. Schaetzle
*Attorney, Agent, or Firm*—Harold R. Patton; Reed A. Duthler

[57] ABSTRACT

A cardiac pacemaker improves battery longevity by automatically providing a safe threshold and an associated pulse width leading to minimum current drain. The pacemaker stores a matrix of current drain characteristics for all of the possible pulse width-voltage pairs, and a revisable strength-duration curve for a patient. Either periodically or as a result of a loss-of-capture episode—whichever occurs first—the pacemaker calculates for each possible pulse width, a new threshold value based upon a measured rheobase and a derived chronaxie. Each threshold is multiplied by a predetermined safety margin. The pacemaker chooses as the pacing stimulation signal, the voltage-pulse width pair having the lowest associated current drain, and satisfying the desired safety margin.

8 Claims, 3 Drawing Sheets

PACEMAKER WHICH ADAPTS TO MINIMIZE CURRENT DRAIN AND PROVIDE DESIRED CAPTURE SAFETY MARGIN

FIELD OF THE INVENTION

The present invention generally relates to "capture" of the heart, here defined as the presence of contractions in the heart in direct response to electrical stimulation signals emanating from an artificial pacemaker ("pacemaker"). Also, the present invention relates to adjusting stimulation signal thresholds for pacemaker energy efficiency.

BACKGROUND OF THE INVENTION

Generally speaking, a cardiac pacemaker is an electrical device used to supplant some or all of an abnormal heart's natural pacing function, by delivering appropriately timed electrical stimulation signals designed to cause the myocardium of the heart to contract or "beat". Stimulation signals usually have well-defined amplitude and pulse width characteristics which can be adjusted to meet physiologic and device power conservation needs.

The strength (amplitude) and duration (pulse width) of the stimulation signals must be of such magnitude that capture is maintained, to prevent serious complications and even death. Yet, it is desirable for these magnitudes not to be higher than is needed for a reasonable safety margin for longer battery life. Chief among the problems is that stimulation signal thresholds necessary for maintaining capture often fluctuate in the short term, and gradually change in the long term. It has been clinically observed that the lowest threshold is observed immediately after implantation of the pacemaker (the acute threshold). Inflammation in the tissue around the tip of the stimulation electrode requires greater energy to propagate the stimulation signals, thereby driving the threshold up sharply during the first two to six weeks to its highest level (the peak threshold). Some of the inflammation reduces over the long-term, to lower the threshold below the peak level—the chronic threshold. However, the chronic threshold does not reduce to the acute level, since some permanent fibrous tissue, requiring greater energy than non-fibrous tissue for signal propagation, remains around the electrode tip. In the short-term, thresholds may decrease with exercise, for example, and may increase with various activities, including sleep.

Some prior art implantable pulse generators (IPGs) which serve as cardiac pacemakers have an automatic capture feature to maintain capture or restore capture after a loss-of-capture episode, without the need for clinical or patient intervention. In addition, some of these IPGs have an automatic threshold-seeking feature, which, either after capture restoration or periodically, seek the lowest "safe" voltage level of the stimulation signal for energy efficiency. That is, the voltage of the stimulation signal is lowered to the newly detected threshold voltage plus a safety margin, rather than using an unnecessarily high stimulation signal voltage level.

However, a lower voltage does not necessarily mean less battery consumption, as a lower voltage in some cases may have an increase in current drain, which has been shown to have a more direct deleterious effect upon battery longevity (of typical pacemakers) than voltage.

SUMMARY OF THE INVENTION

In view of the foregoing, the main object of the present invention is to provide a cardiac pacemaker having an automatic threshold-seeking feature in which current drain is minimized.

In order to satisfy the above object and others, the present invention provides a pacemaker system capable of automatically seeking stimulation signal thresholds to increase power efficiency, the system at least including:
  current drain storing means for storing current drain characteristics associated with an array of voltage-pulse width pairs based upon the physiology of a patient;
  threshold generating means for generating a threshold for each possible pulse width; and
  pacing signal selecting means for associating each generated threshold with a current drain characteristic stored in the current drain storing means, and for selecting as a pacing signal, the generated threshold having the lowest current drain associated therewith.

The present invention also provides in a pacemaker, an automatic stimulation signal threshold seeking method for automatically seeking stimulation signal thresholds to increase power efficiency, the method at least including the steps of:
  in a current drain storing means, storing current drain characteristics associated with an array of voltage-pulse width pairs based upon the physiology of a patient;
  generating a threshold for each possible pulse width;
  associating each generated threshold with a current drain characteristic stored in the current drain storing means; and
  selecting as a pacing signal, the generated threshold having the lowest current drain associated therewith.

The details of the present invention will be revealed in the following description, with reference to the attached drawing.

BRIEF DESCRIPTION OF THE DRAWING

The various figures of the drawing are briefly described as follows.

DETAILED DESCRIPTION OF THE INVENTION

PART I. DESCRIPTION OF PACEMAKER DEVICE.

Figure 1:
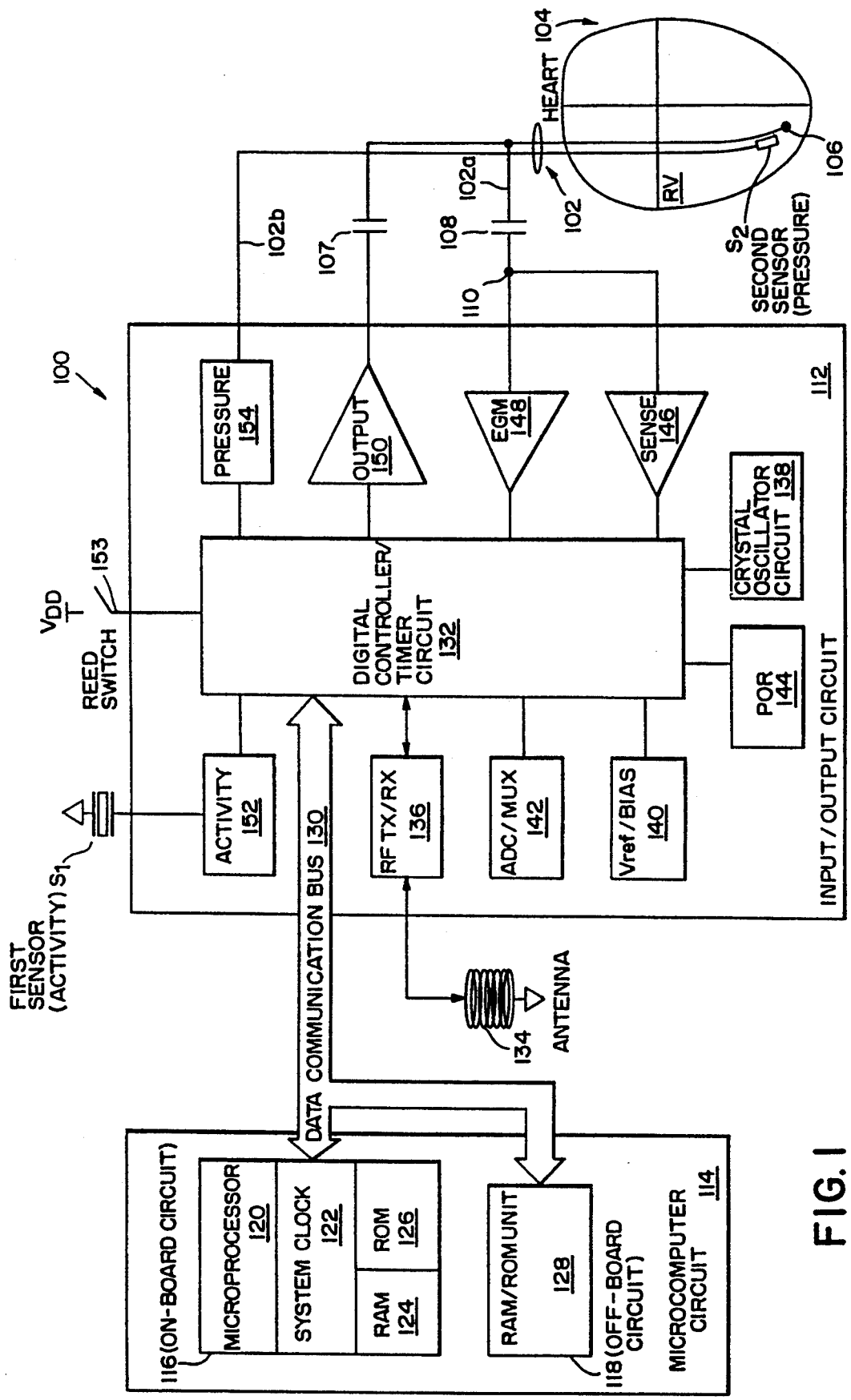
FIG. 1 is a schematic block diagram of a multi-sensor, rate-responsive, single chamber IPG capable of subsuming the present invention.

FIG. 1 is a block circuit diagram illustrating a multi-programmable, implantable, single-chamber, bradycardia pacemaker 100 capable of carrying out the present invention. This figure and related figures not presented in this letters patent are described in U.S. Pat. No. 5,154,170, issued Oct. 13, 1992, and titled OPTIMIZATION FOR RATE RESPONSIVE CARDIAC PACEMAKER, which patent is hereby incorporated by reference. Although the present invention is described in conjunction with a microprocessor-based architecture, it will be understood that it could be implemented in digital logic-based, custom integrated circuit (IC) architecture, if desired. It will also be understood that the present invention may be implemented in dual-chamber pacemakers, cardioverters, defibrillators and the like.

In the preferred embodiment of FIG. 1, pacemaker 100 includes two sensors, namely, $S_1$ and $S_2$, each of which provide a sensor output which varies as a function of a measured parameter that relates to the metabolic requirements of the patient. Since each sensor output can be utilized by pacemaker 100 to control its pacing rate, each sensor output is herein referred to as a rate-control parameter (RCP). Examples of an RCP include, for example, physical activity of the body, right ventricular blood pressure and the change of right ventricular blood pressure over time, venous blood temperature, venous blood oxygen saturation, respiration rate, minute ventilation, and various pre- and post-systolic time intervals measured by impedance or pressure sensing within the right ventricle of the heart.

In the preferred embodiment, first sensor $S_1$ comprises an activity sensor, such as a piezoelectric sensor of the type disclosed in U.S. Pat. No. 4,428,378 issued to Anderson et al., entitled "Rate Adaptive Pacer", which is held by the same assignee as the present invention and which is incorporated herein by reference. First sensor $S_1$ thus measures a rate-control parameter related to physiologic forces associated with body activity ($RCP_{act}$), and provides a first sensor output ($Output_{act}$) which is proportional to the patient's activity. Also in the preferred embodiment, second sensor $S_2$ comprises a dynamic pressure sensor, such as the type disclosed in U.S. Pat. No. 4,485,813 issued to Anderson et al., entitled "Implantable Dynamic Pressure Transducer System", which is held by the same assignee as the present invention and which is incorporated by herein by reference. Second sensor $S_2$ thus measures a rate-control parameter related to changes in fluid pressure in the heart associated with its mechanical activity and contractility ($RCP_{press}$), and provides a second sensor output ($Output_{press}$) which is proportional to the magnitude of the change in fluid pressure in the patient's heart. In the preferred embodiment, second sensor output $S_2$ is processed to derive a peak positive time derivative of the fluid pressure applied to the pressure sensor $S_2$ within the right ventricle of the patient's heart (i.e., $dP/dt_{max}$).

Pacemaker 100 is schematically shown electrically coupled via a pacing lead 102 to a patient's heart 104. Lead 102 includes an intracardiac electrode 106 and second sensor $S_2$ which are located near the distal end of lead 102 and positioned within the right ventricle (RV) of the patient's heart. Lead 102 can carry either unipolar or bipolar electrodes as is well known in the art. In the preferred embodiment, the lead 102 which couples pacemaker 100 to the ventricular endocardium can comprise a steroid-tipped, unipolar lead with an integral pressure transducer of the type described above. Electrode 106 is coupled via suitable lead conductor 102a through input filter capacitor 108 to node 110 and to the input terminals of an Input/Output Circuit shown at block 112. Output from first sensor $S_1$ is coupled to Input/Output Circuit 112. Output from second sensor $S_2$ is also coupled to Input/Output Circuit 112 via suitable lead conductor 102b.

Input/Output Circuit 112 contains the operating input and output analog circuits for digital controlling and timing circuits necessary for the detection of electrical signals derived from the heart, such as the cardiac electrogram, output from the first sensor output $S_1$, and output from the second sensor output $S_2$, as well as for the application of stimulating pulses to the heart to control its rate as a function thereof under the control of software-implemented algorithms in a Microcomputer Circuit shown at 114.

Microcomputer Circuit 114 comprises an On-Board Circuit 116 and an Off-Board Circuit 118. On-Board Circuit 116 includes a microprocessor 120, a system clock 122, and on-board RAM 124 and ROM 126. Off-Board Circuit 118 includes an off-board RAM/ROM Unit 128. Microcomputer Circuit 114 is coupled by Data Communication Bus 130 to a Digital Controller/Timer Circuit shown at 132. Microcomputer Circuit 114 may be fabricated of custom IC devices augmented by standard RAM/ROM components.

It will be understood by those skilled in the art that the electrical components represented in FIG. 1 are powered by an appropriate implantable-grade battery power source (not shown).

An antenna 134 is connected to Input/Output Circuit 112 for purposes of uplink/downlink telemetry through a radio frequency (RF) Transmitter/Receiver Circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device", which is held by the same assignee as the present invention and which is incorporated herein by reference. A reed switch 153 is connected to Input/Output Circuit 112 to enable patient follow-up via disabling the sense amplifier 146 and enabling telemetry and programming functions, as is known in the art.

A Crystal Oscillator Circuit 138, typically a 32,768 Hz crystal-controlled oscillator, provides main timing clock signals to Digital Controller/Timer Circuit 132. A Vref/Bias Circuit 140 generates a stable voltage reference and bias currents for the analog circuits of Input/Output Circuit 112. An ADC/Multiplexer Circuit (ADC/MUX) 142 digitizes analog signals and voltages to provide telemetry and replacement time-indicating or end-of-life function (EOL). A Power-on-Reset Circuit (POR) 144 functions to initialize the pacemaker 100 with programmed values during power-up, and reset the program values to default states upon the detection of a low battery condition or transiently in the presence of certain undesirable conditions such as unacceptably high EMI, for example.

The operating commands for controlling the timing of the pacemaker depicted in FIG. 1 are coupled by bus 130 to Digital Controller/Timer Circuit 132 wherein digital timers set the overall escape interval of the pacemaker, as well as various refractory, blanking and other timing windows for controlling the operation of the peripheral components within Input/Output Circuit 132.

Digital Controller/Timer Circuit 132 is coupled to a sense amplifier (SENSE) 146 and an electrogram (EGM) amplifier 148 for receiving amplified and processed signals picked up from electrode 106 through lead conductor 102a and capacitor 108 representative of the electrical activity of the patient's heart 104. SENSE amplifier 146 produces a sense event signal for re-setting the escape interval timer within Circuit 132. The electrogram signal developed by EGM amplifier 148 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention and which is incorporated by herein by reference. An output pulse generator 150 provides the pacing stimulus to the patient's heart 104 through an output capacitor 107 and lead 102 in response to a paced trigger signal developed by Digital Controller/Timer Circuit 132 each time the escape interval times out, or an externally transmitted pacing command has been received, or in response to other stored commands as is well known in the pacing art.

Digital Controller/Timer Circuit 132 is coupled to a processing/amplifying circuit (ACTIVITY) 152 for receiving amplified and processed sensor output (Output$_{act}$) from first sensor S$_1$ and associated ACTIVITY circuitry which is representative of activity. Digital Controller/Timer Circuit 132 is coupled to a processing/amplifying circuit (PRESSURE) 154 for receiving amplified and processed sensor output (Output$_{press}$) from second sensor S$_2$ through lead conductor 102b representative of changes in fluid pressure in the patient's heart 104, for use in rate response control, and others functions as desired.

In a preferred embodiment of the present invention, pacemaker 100 is capable of operating in various non-rate-responsive modes which include VVI, VOO and VVT, as well as corresponding rate-responsive modes of VVIR, VOOR and VVTR. Further, pacemaker 100 can be programmably configured to operate such that it varies its rate only in response to one selected sensor output, or in response to both sensor outputs, if desired (i.e., utilizing either or both of Output$_{act}$ or Output$_{press}$).

PART II. DEFINITIONS.

For purposes of describing this invention, a definition of additional relevant terms follows:

Detection Window—A 170 mSec window beginning 30 mSec after a paced or sensed event used to detect the presence of a pressure signal indicative of cardiac contraction.

Loss-of-Capture (LOC)—Processing by pacemaker 100 detects the absence of a pressure signal in the detection window after a paced event. This lack of stimulated cardiac contraction is labeled Loss-of-Capture.

Lower Rate (LR)—A value supplied by the clinician which establishes a lower boundary on the pacing rate. If the sensors are disabled, or their sensor outputs are not large enough to increase rate, the lower rate is the stimulus rate. With rate response, the allowed programmable values for LR range from 40 pulses per minute (ppm) to 100 ppm at 1 ppm intervals.

Metric—The programmed (selected) output stimulus parameter (pulse width or pulse amplitude) selected to be modified in the response to Loss-of-Capture and during the Recovery sequence.

Non-Metric—The non-selected output stimulus parameter (pulse width or pulse amplitude). The non-metric parameter is changed only at the maximum output stimulus during response to Loss-of-Capture.

P$_{max}$—Processing by pacemaker 100 determines the maximum signal level in the pressure waveform from pressure circuit 154 during a detection window.

P$_{min}$—Processing by pacemaker 100 determines the minimum signal level in the pressure waveform from pressure circuit 154 during a detection window.

Pulse Pressure Average (PRESS.AVG)—Dynamic pressure sensor S$_2$ is disposed in the right ventricle (RV) of the patient's heart to sense fluid pressure therein (RCP$_{press}$), and to provide a sensor output (Output$_{press}$) related to changes in the fluid pressure associated with the heart's mechanical activity and contractility. Processing by pacemaker 100 of Output$_{press}$ yields a peak pulse pressure (PRESS.PK) which is proportional to the magnitude of such RV pressure changes. Each sensed or paced RV event will yield a peak pulse pressure signal. In the preferred embodiment, a running average of the last 16 valid PRESS.PK values are used to determine an average peak pulse pressure value, referred to as the "PRESS.AVG". Pacemaker 100 tests for validity of each peak pulse pressure value on a sample-by-sample basis, based upon the requirement that the sampled PRESS.PK value must be equal to or greater than, 4 mm Hg. Values below this validity threshold are ignored. Once determined, PRESS.AVG is used to detect capture on a cycle-to-cycle basis.

Recovery—Pacemaker 100 automatically attempts to adjust output stimulus parameters 1 hour after a Loss-of-Capture sequence. The metric parameter is adjusted in small increments toward it's programmed value.

Response to LOC—Pacemaker 100 automatically responds to a LOC by increasing the output pulse width and/or amplitude in a controlled response to enable rapid restoration of cardiac stimulation.

Threshold—A programmable threshold of continuously averaged peak pulse pressure value based upon a percentage of this stored peak value. The programmable range is 25–75% in 12.5% steps.

Upper Rate (UR)—A value supplied by the clinician which limits the maximum stimulation rate when the rate responsive modes for activity, pressure, or both combined, are in effect, or when response to loss-of-capture pacing is occurring such that the pacing rate generated by pacemaker 100 does not become hemodynamically excessive. The allowed programmable values range from 100 ppm to 175 ppm at 5 ppm intervals, provided UR must also be at least 20 ppm greater than Lower Rate (LR) and Resting Rate (REST.RATE).

PART III. SENSORS.

A brief description of measurement of the rate control parameter for activity (RCP$_{act}$) now follows. The activity sensor S$_1$ sensor employed is a piezoelectric crystal transducer of the type described in the above-mentioned '378 Anderson et al. patent, which is mounted to the interior surface of the pacemaker can as disclosed therein. Sensor S$_1$ generates a sensor output (Output$_{act}$) due to deflection of the pacemaker can as a result of compression waves within the body caused by physical movement of the body. Processing by ACTIVITY circuit 152 is performed, such that each event in which the amplitude of Output$_{act}$ exceeds a programmed Activity Threshold (ACT.THRESH) is then counted and retained in an Activity Count (ACT.COUNT) of pacemaker 100. ACT.COUNT is used to calculate the activity-based Target Rate (STR$_{act}$) on a cycle-to-cycle basis.

A brief description of measurement of the rate control parameter for pressure ($RCP_{press}$) now follows. The pressure sensor $S_2$ sensor employed is a dynamic pressure sensor of the type described in the above-mentioned '813 Anderson et al. patent. Sensor $S_2$ is disposed in the right ventricle (RV) of the patient's heart to sense fluid pressure therein ($RCP_{press}$), and to provide a sensor output ($Output_{press}$) related to changes in the fluid pressure associated with the heart's mechanical activity and contractility. Processing by PRESSURE circuit 154 of $Output_{press}$ yields a peak positive first time derivative thereof ($dP/dt_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dP/dt_{max}$ value, referred to as the "Pressure (dP/dt) Average" or "dP/dt.AVG". Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value associated with the patient's Resting Rate (REST.PRESS). In the preferred embodiment, this validity range is defined as $dP/dt_{max}$ values between 25% to 400% of REST.PRESS. Values outside this validity range are ignored. Once determined, PRESS.AVG is used to calculate the pressure-based Sensor Target Rate ($STR_{press}$) on a cycle-to-cycle basis.

It will be understood, however, that the present invention can be practiced with more than two sensors, or with sensors of a type other than the ones above described. In the preferred embodiment, however, various advantages are obtained by the use of the particular sensors in the specific combination stated above.

For example, an activity-based sensor provides a fast and repeatable response to physical activity. Sensors of this type have been exhaustively reported in clinical literature, and their safety and efficacy are well-documented. Additionally, such sensors offer the advantage of being less affected by changes in a patient's health or disease status, and thus provide more predictable behavior over time. However, there are also theoretical and practical limitations to the behavior of activity sensors. For example, they respond only to physical activity. Therefore, patients undergoing other types of physiological stresses which would normally evoke a heart rate response, such as thermal stress associated with normal exposure to wide variations in ambient temperature, or postural stress associated with changing from lying down to an erect position, will tend to obtain only very limited rate adjustment and their adjustment to such stresses will thus be less than entirely adequate. Additionally, the time course of rate recovery after an activity event tends to be limited by the design constraints of the pacemaker system which are not generally capable of providing a highly physiologically-based recovery function.

Consequently, the preferred embodiment also incorporates a dynamic pressure sensor for continuous measurement of cardiac pressures on a beat-by-beat basis. This sensor provides for more physiological responses than activity alone, and helps to complement the rate response provided by the activity sensor. The sensed physiologic variable in this system comprises the rate of increase in pressure within the right ventricle of the heart (i.e., a peak positive dP/dt). This variable is related to the vigor of contraction of the cardiac muscle, which in turn is regulated by the autonomic nervous system. Thus, any stress which elicits a response by the autonomic nervous system in the patient (and would cause a heart rate response in a normal individual), will also yield a heart rate response in the patient by means of the pacemaker system of the present invention. Additionally, the time course of recovery of the cardiac pressure following stresses follows the physiologic time course determined by the status of the autonomic nervous system, such that the present device will provide for pacing rate recovery which is more physiological than that which can be provided by activity sensors alone.

It can thus be appreciated that the particular sensor combination described above yields significantly improved rate response function for pacemaker 100.

PART IV. THRESHOLD-SEEKING AND CURRENT MINIMIZATION FEATURES.

Specific details of the threshold-seeking and current minimization features of the present invention follow below. Of related interest is U.S. patent application Ser. No. 07/958,194, filed Oct. 7, 1992, now U.S. Pat. No. 5,320,643, for AUTOMATIC CARDIAC CAPTURE RESTORATION AND THRESHOLD-SEEKING METHOD AND APPARATUS, which application is also assigned to the assignee of the present application, and which application is also expressly incorporated by reference. That application provides additional details about auto-capture and threshold-seeking functions which may be modified to operate in conjunction with the present invention.

Figure 2:
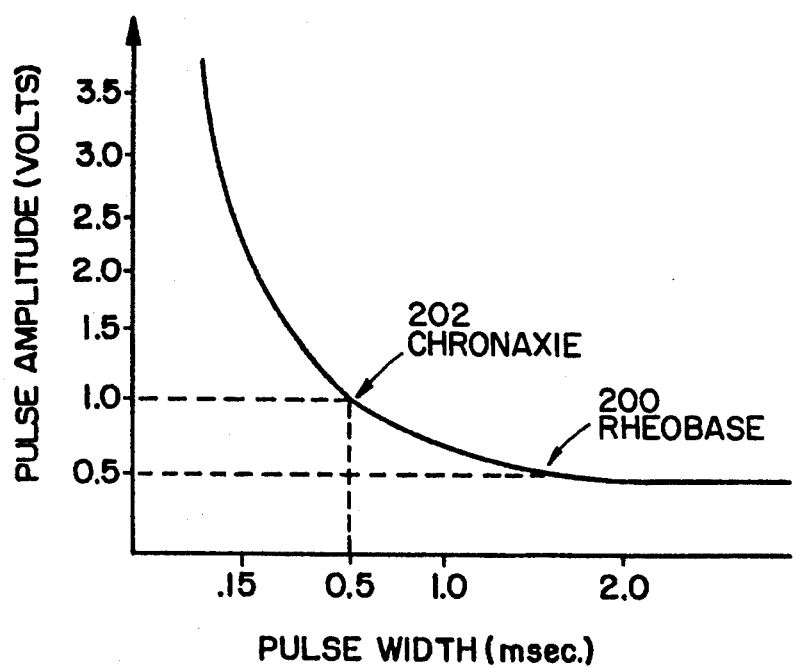
FIG. 2 is a typical strength-duration curve for cardiac stimulation signals.

FIG. 2 shows a typical strength-duration curve for electrical stimulation of myocardial tissue plotted as pulse amplitude in volts versus pulse width in milliseconds. The graph shows, inter alia, that the threshold increases with a decreasing pulse width, and thus decreases with an increasing pulse width, except that beyond the rheobase 200, no further reductions in the threshold can be achieved. Thus, increasing the pulse width beyond 2 milliseconds in the example shown still requires a threshold of 0.5 volts. Also included on the graph for illustrative purposes is the chronaxie 202, a measure of myocardial excitability, which is the point representing the lowest pulse width needed to have twice the rheobasic threshold. It is well known in the art to provide a safety margin between the actual amplitudes of stimulation signals and the thresholds from the strength-duration curve. However, as previously stated, the amount of safety margin may change over time and must be balanced against the need to maximize battery life, as increased amplitude and pulse width will cause a greater battery energy consumption.

Physiological changes in the patient may alter the thresholds from the initial programmed value or values, and can lead to loss of capture, with inadequate amplitude or pulse width. The pacemaker 100 is capable of detecting loss of capture via the pressure sensor $S_2$, described supra with reference to FIG. 1, in the form of low pulse pressure values.

Figure 3:
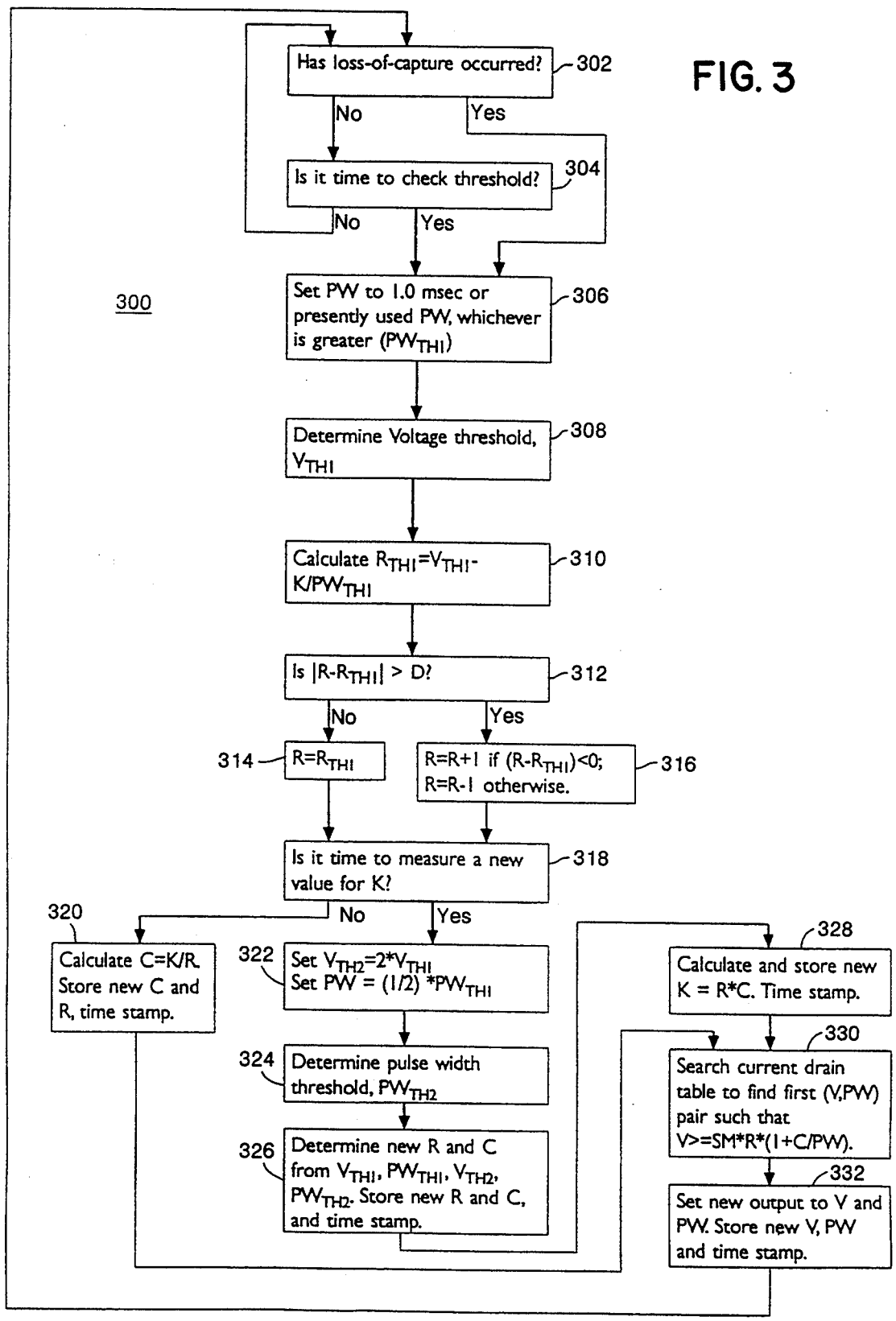
FIG. 3 is a flow chart illustrating the present invention's threshold-seeking and current drain minimization program/routine.

FIG. 3 shows a flow chart detailing the programmed steps 300 used by the pacemaker 100 for selecting a pacing threshold with minimum current drain.

Prior to unassisted operation of the pacemaker 100, the following are stored in memory: the desired capture safety margin (for example, 2 or 2.5 times); values representing the patient's strength-duration curve; and a matrix of the pacemaker's current drain characteristics.

The matrix consists of a specific current drain associated with each voltage and pulse width pair, and is ordered from lowest to higher current drains.

A new pacing threshold is selected either at scheduled intervals (Step 304), or after the detection of a loss-of-capture episode (Step 302), whichever occurs first. A study at Robert Bates Cardiology Center in Bradenton, Fla. during 1990-91, demonstrated that the strength-duration curve for an individual patient is relatively constant, and further that even when the rheobase R and the chronaxie C vary individually, the product of the two is relatively constant. That study is published in the article "Chronic Stimulation Threshold Stability"; M. Sweesy, R. Forney. R. Batey, R. Powell; Presented at CardioStim '92, Nice, France. The constant K can be calculated and stored in memory based upon initial measured R and C values. Thereafter, new R values can be measured and new C values can be calculated by dividing K by R (i.e., C=K/R). Assuming that the patient's condition remains relatively stable, a new strength-duration curve can be calculated as follows, using the Lapicque approximation:

$$V_{TH} = R(1 + C/PW) \quad \text{(Equation 1)}$$

where $V_{TH}$ is the threshold voltage at a given pulse width PW. After setting PW to 1.0 msec (a design choice) or the present pulse width value, whichever is greater (Step 306), represented by the symbol $PW_{TH1}$, the threshold voltage $V_{TH1}$ is measured (Step 308).

The corresponding rheobase $R_{TH1}$ is calculated (Step 310), and the absolute value of the difference between the stored rheobase R and the newly calculated rheobase $R_{TH1}$ is compared to D, a predetermined maximum allowed rheobase change (Step 312). If $R - R_{TH1}$ is less than or equal to D, the stored rheobase R is replaced by $R_{TH1}$ (Step 314). If $R - R_{TH1}$ is greater than D, then R is set equal to $R+1$ for the case where $R - R_{TH1}$ is a negative number, and R is set equal $R-1$ for the case where $R - R_{TH1}$ is not a negative number (Step 316).

The pacemaker 100 then determines whether it is time to measure a new constant K based upon whether a predetermined time period has expired (Step 318). If it is not time to measure a new constant K, a new chronaxie C is calculated, and the rheobase R and chronaxie C are stored with time stamps (markers indicating the time at which events occurred—in this case, when the calculations were made) at Step 320. The program then advances to Step 330.

If it is time to measure a new value for the constant K, the program advances to Step 322 where a second voltage threshold $V_{TH2}$ is calculated by doubling $V_{TH1}$, and the pulse width PW is set equal to one-half of $PW_{TH1}$. At Step 324, the pulse width threshold $PW_{TH2}$ is measured by applying the formula used in Step 306. At Step 326, a new rheobase R and a new chronaxie C are calculated using the following equations:

$$R = \frac{(V_{TH2} * PW_{TH2}) - (V_{TH1} * PW_{TH1})}{PW_{TH2} - PW_{TH1}} \quad \text{(Equation 2)}$$

$$C = \frac{(PW_{TH1} * PW_{TH2}) * (V_{TH1} - V_{TH2})}{(PW_{TH2} * V_{TH2}) - (PW_{TH1} * V_{TH1})} \quad \text{(Equation 3)}$$

The new R and C values are then stored with time stamps. Additionally, a new value for the constant K is calculated and stored with a time stamp at Step 328.

The pulse width-voltage pair having the lowest current drain characteristics is chosen from the memory matrix according to the equation shown in step 330 (i.e., $V \geq SM*R*(1+C/PW)$). The new values of V and PW are stored in memory with time stamp, and used in the stimulation pulses. The pacemaker 100 then returns to the beginning Step 302 of the program 300, to start the threshold-seeking process anew.

Thus it has been described supra., a pacemaker for selecting as its pacing signal, the safety-margined voltage threshold having the lowest current drain, as well as its associated pulse width.

As a diagnostic tool during a patient's follow-up visit to a clinician, the series of strength-duration curves with associated dates and times of calculations are stored in memory to indicate a trend of physiological changes in the patient, and possible pacing lead problems or drug complications.

As a safety feature, the present invention includes dampening, to limit the amount a new strength-duration curve can vary from the previous one. When a new R value varies by more than a predetermined maximum amount, the pacemaker 100 only stores the value representing the maximum amount of allowable change. This eliminates spurious test results which can lead to an inadvertent loss-of-capture episode.

Variations and modifications to the present invention are possible given the above disclosure. However, such variations and modifications are intended to be within the scope of the invention claimed by this letters patent.

We claim:

1. A cardiac pacemaker, comprising:
   a pacing pulse generator;
   means for defining a set of available pulse amplitude and pulse width combinations;
   means for selecting a desired pulse width and amplitude combination from said set of available pulse amplitude and width combinations; and
   control means for causing said pulse generator to generate pacing pulses at said selected pulse amplitude and pulse width combination;
   wherein said selecting means comprises:
      means for determining a current drain associated with delivery of pacing pulses at each of said available pulse amplitude and pulse duration combinations;
      means for determining a strength/duration relationship for stimulation of a patient's heart;
      means for defining a desired safety margin;
      means for determining which of said available pulse width and amplitude combinations provide said desired safety margin, based on said strength/duration relationship; and
      means for selecting from those available pulse amplitude and pulse width combinations which provide said safety margin, the one of said available pulse amplitude and pulse width combinations which has a minimum current drain associated therewith.

2. A cardiac pacemaker according to claim 1 wherein said means for determining a strength/duration relationship comprises means for updating said determined strength/duration relationship.

3. A cardiac pacemaker according to claim 2 wherein said means for updating said determined strength/duration relationship comprises means for preventing said updated strength/duration relationship from varying from a predetermined strength/duration relationship by more than a predetermined amount.

4. A method of cardiac pacing, comprising:
defining a set of available pulse amplitude and pulse width combinations;
selecting a desired pulse width and amplitude combination from said set of available pulse amplitude and width combinations; and
generating pacing pulses at said selected pulse amplitude and pulse width combination;
wherein said selecting step in turn comprises:
determining a current drain associated with delivery of pacing pulses at each of said available pulse amplitude and pulse duration combinations;
determining a strength/duration relationship for stimulation of a patient's heart;
defining a desired safety margin;
determining which of said available pulse width and amplitude combinations provide said desired safety margin, based on said determined strength/duration relationship; and
selecting from those available pulse amplitude and pulse width combinations which provide said safety margin, the one of said available pulse amplitude and pulse width combinations which has a minimum current drain associated therewith.

5. A cardiac pacemaker according to claim 4 wherein method further comprises the step of updating said determined strength/duration relationship.

6. A cardiac pacemaker according to claim 5 wherein said step of updating said determined strength/duration relationship comprises the step of preventing an updated strength/duration relationship from varying more than a predetermined amount from a previously determined strength/duration relationship.

7. A cardiac pacemaker, comprising:
a pacing pulse generator;
means for defining a set of available pulse amplitude and pulse width combinations;
means for selecting a desired pulse width and amplitude combination from said set of available pulse amplitude and width combinations; and
control means for causing said pulse generator to generate pacing pulses at said selected pulse amplitude and pulse width combination;
wherein said selecting means comprises:
means for determining a strength/duration relationship for stimulation of a patient's heart;
means for updating said determined strength/duration relationship, comprising means for preventing an updated strength/duration relationship from varying more than a predetermined amount from a previously determined strength/duration relationship;
means for defining a desired safety margin; and
means for selecting one of said available pulse width and amplitude combinations providing said desired safety margin, based on said updated determined strength/duration relationship.

8. A method of cardiac pacing, comprising:
defining a set of available pulse amplitude and pulse width combinations;
selecting a desired pulse width and amplitude combination from said set of available pulse amplitude and width combinations; and
generating pacing pulses at said selected pulse amplitude and pulse width combination;
wherein said selecting step comprises:
determining a strength/duration relationship for stimulation of a patient's heart;
updating said determined strength/duration relationship, said updating step comprising the step of preventing an updated strength/duration relationship from varying more than a predetermined amount from a previously determined strength/duration relationship;
defining a desired safety margin; and
selecting one of said available pulse width and amplitude combinations providing said desired safety margin, based on said updated determined strength/duration relationship.

* * * * *